United States Patent
Parmar (10) Patent No.: US 10,300,246 B2
(45) Date of Patent: May 28, 2019

(54) EM GUIDANCE DEVICE FOR A DEVICE ENABLED FOR ENDOVASCULAR NAVIGATION PLACEMENT INCLUDING A REMOTE OPERATOR CAPABILITY AND EM ENDOLUMINAL IMAGING TECHNIQUE

(76) Inventor: Jaywant Philip Parmar, Morro Bay, CA (US)

( * ) Notice: Subject to any disclaimer, the term of this patent is extended or adjusted under 35 U.S.C. 154(b) by 577 days.

(21) Appl. No.: 13/593,502

(22) Filed: Aug. 23, 2012

(65) Prior Publication Data
US 2013/0072943 A1 Mar. 21, 2013

Related U.S. Application Data

(60) Provisional application No. 61/526,682, filed on Aug. 23, 2011.

(51) Int. Cl.
*A61M 25/01* (2006.01)
*A61B 5/06* (2006.01)
*A61M 25/09* (2006.01)
*A61B 34/20* (2016.01)
(Continued)

(52) U.S. Cl.
CPC .......... *A61M 25/0105* (2013.01); *A61B 5/062* (2013.01); *A61B 34/20* (2016.02); *A61M 25/0127* (2013.01); *A61M 25/09041* (2013.01); *A61B 2017/00398* (2013.01); *A61B 2017/22038* (2013.01); *A61B 2017/22084* (2013.01); *A61B 2017/22091* (2013.01); *A61B 2034/2051* (2016.02); *A61M 2025/0166* (2013.01);
(Continued)

(58) Field of Classification Search
CPC .......... A61M 25/0105; A61M 25/0127; A61M 25/09041; A61B 19/5244
See application file for complete search history.

(56) References Cited

U.S. PATENT DOCUMENTS 3,051,164 A * 8/1962 Trexler ................ A61G 10/005
119/417
5,758,660 A * 6/1998 Lokken .............. A61M 25/0111
128/877
7,992,573 B2 8/2011 Wilson
(Continued)

FOREIGN PATENT DOCUMENTS

RU 2218191 12/2003
WO WO2010093922 8/2010

OTHER PUBLICATIONS

International Preliminary Report on Patentability, dated Feb. 25, 2014.
(Continued)

*Primary Examiner* — Thomas M McEvoy
(74) *Attorney, Agent, or Firm* — Frank Rosenberg (57) ABSTRACT

A method and system for placing a device enabled for endovascular navigation, specifically a PICC catheter, and more broadly any device which is manipulated in over the wire or monorail fashion. Variants of the system comprise a guidewire for navigating through a patient's vasculature, having an electromagnetic (EM) based tracking components at or near the a leading end of the guidewire; an EM positioning field generator configured on a reference gantry; a computer and display configured to output position information of the guidewire leading end; and a servomotor delivery system actuator, mechanically coupled to the guidewire and configured for controlling the position of the guidewire.

13 Claims, 5 Drawing Sheets

(51) Int. Cl.
*A61B 17/00* (2006.01)
*A61B 17/22* (2006.01)

(52) U.S. Cl.
CPC ............ *A61M 2025/09175* (2013.01); *A61M 2025/09183* (2013.01)

(56) References Cited

U.S. PATENT DOCUMENTS

| | | |
|---|---|---|
| 2003/0208188 A1 | 11/2003 | Ritter et al. |
| 2004/0097805 A1* | 5/2004 | Verard ............... A61B 1/00071 600/428 |
| 2006/0041245 A1* | 2/2006 | Ferry et al. ................... 604/510 |
| 2007/0182729 A1* | 8/2007 | Klingenbeck-Regn et al. ............ 345/418 |
| 2008/0231264 A1* | 9/2008 | Krueger et al. ......... 324/207.22 |
| 2009/0076445 A1 | 3/2009 | Furnish |
| 2009/0131798 A1 | 3/2009 | Minar |
| 2011/0257661 A1 | 10/2011 | Choi |
| 2013/0096589 A1 | 4/2013 | Spencer |

OTHER PUBLICATIONS

International Search Report from PCT/US15/046610 dated Feb. 19, 2016.
Written Opinion from PCT/US15/046610 dated Feb. 19, 2016.

\* cited by examiner

EM GUIDANCE DEVICE FOR A DEVICE ENABLED FOR ENDOVASCULAR NAVIGATION PLACEMENT INCLUDING A REMOTE OPERATOR CAPABILITY AND EM ENDOLUMINAL IMAGING TECHNIQUE

CROSS-REFERENCES TO RELATED APPLICATIONS

The present application claims priority from U.S. Provisional Application Ser. No. 61/526,682 filed on Aug. 23, 2011, which is hereby incorporated herein by reference in its entirety.

TECHNICAL FIELD

The present invention, in some embodiments thereof, relates to a method and system for positioning a medical device enabled for endovascular navigation within a patient, and more particularly, some embodiments relate to a PICC positioning system and imaging system.

BACKGROUND OF THE INVENTION

The following document outlines a method and system for placing devices enabled for endovascular navigation, and in some embodiments relate to the accurate positioning of peripherally inserted central venous catheters (PICC) and positioning the tip accurately in the optimal location within the superior vena cava (SVC), through the use of electromagnetic tip tracking systems. In general, the method can enable a variety of procedures and internal imaging techniques that rely on electromagnetic position probes being manipulated within the body in reference to surface anatomic markers only. These sorts of hospital based procedures are routinely performed without real time imaging, requiring post procedural radiographic confirmation and possible repeat blind manipulation and re-imaging. Present methods operate through an iterative process of initial device placement, imaging, device manipulation and re-imaging, and eventually a position of the intracranial, intravenous, endotracheal or endoenteric instrument deemed acceptable is achieved. Often, due to the tedious iterative process, suboptimal or non-ideal positioning is deemed acceptable by the medical system. Uncommonly, real time fluoroscopic positioning relative to radiographic landmarks is required to achieve proper positioning. These radiographic landmarks are most often and most reliably related to the bony anatomy which is easily appreciated on physical examination (e.g., the clavicles, sternal notch, xyphoid process, rib cage margins, acromion processes, iliac crests, and symphysis pubis, among other bony surface anatomic landmarks.

It would be advantageous to have a system, such as the present invention, wherein: optimal placement is accurately achieved with image guidance using no x-rays; the placement occurs with creation of a patient specific image representation of the venous anatomy that serves as documentation and is exported to radiology picture archiving communication systems (PACS) in the radiological standard Digital Imaging and Communications in Medicine (DICOM) format; and there can be a high level of hands-on physician (e.g. interventional radiologist) operation during the most critical portions of the placement procedure with high operational efficiencies provided through telecommunication and remote actuation technologies.

BRIEF SUMMARY OF EMBODIMENTS OF THE INVENTION

The present invention relates to a system and method for PICC positioning inside the internal vasculature of a patient anatomy, comprising an electromagnetic guidance system and microcomputer display configured for real time or on the fly mapping of the venous system in reference to surface anatomical markers with optional remote operator capabilities.

(1) An aspect of some embodiments to the present invention relates to A system for accurate positioning of a device enabled for endovascular navigation, comprising: one of a catheter or guidewire or combination for navigating through a patient's vasculature, having an electromagnetic (EM) based tracking components at or near the leading end of the device; an EM positioning field generator configured on a reference gantry; a computer and display configured to output position information of the leading end of one of a guidewire or a catheter or a combination thereof; and a servomotor delivery system actuator, mechanically coupled to the one of a guidewire or catheter or combination thereof, and configured for controlling the position the guidewire or catheter or combination thereof.

(2) In a variant of the system for accurate positioning of a device enabled for endovascular navigation, the device comprises a peripherally inserted central venous catheter (PICC).

(3) In another variant of the accurate PICC positioning system, the guidewire comprises an EM tracker tip with having an angled guidewire tip.

(4) In a further variant of the accurate positioning system, the guidewire is part of a guidewire-catheter system having an integrated tip sensor coil engineered between the catheter and the guidewire such that inductor windings are located within the catheter and a magnetic susceptible and magnetic field focusing ferrite core within the guidewire.

(5) In still another variant of the accurate positioning system, the servomotor has a remote operation interface, configured to receive and carry out commands from a remote location, to manipulate the guidewire and catheter.

(6) In yet a further variant of the accurate positioning system claim 1, wherein the servomotor delivery system actuator, and the mechanical coupling to the one of a guidewire or catheter or combination thereof, is sealed within a sterile enclosure.

(7) In a variant of the accurate PICC positioning system, the EM tracking components comprise a sensor coil integrated into the tip of a PICC, and comprises: a power injectable hemostatic connector hub for contrast administration through the PICC.

(8) In another variant of the accurate positioning system, the system is configured to record anatomy shape data, during placement of the catheter.

(9) In a further variant, the accurate positioning system comprises an intravenous catheter-adapted remote sensor.

(10) In still another variant, a method of accurate catheter placement comprises: navigating a guidewire configured with an EM tracking device located on a leading end of the guidewire to a desired location, in the presence of an EM field established by an EM positioning field generator configured on a reference gantry, and actuating the guidewire via a servomotor actuator system mechanically coupled to the guidewire and to a catheter, while the catheter is parked; computing a length of the catheter to be generated, based on a distance navigated by the guidewire; advancing a trimming mechanism over the parked catheter; actuating the trimming mechanism to generate a catheter having the computed length; and advancing the catheter with the computed length over the guidewire.

(11) In yet a further variant of the method of accurate catheter placement, the step of actuating the trimming mechanism, comprises cutting the catheter with a blade oriented transverse to the catheter.

(12) In another variant of the method of accurate catheter placement, the step of actuating the trimming mechanism comprises cutting the catheter longitudinally, parallel to the axis of the catheter.

(13) In a further variant, the method of accurate catheter placement comprises simultaneously acquiring anatomy shape date while navigating the guidewire or catheter or combination thereof to a desired location.

(13) In still another variant, a physician operator workflow for placement of a PICC in patients, comprises: placing a valved vascular introducer sheath into a vein of a plurality of patients; mechanically linking an actuator of a system for accurate positioning of a PICC, wherein the system comprises: a PICC guidewire for navigating through a patient's vasculature, having an electromagnetic (EM) based tracking components at or near the a leading end of the guidewire; an EM positioning field generator configured on a reference gantry; a computer and display configured to output position information of the guidewire leading end; and a servomotor delivery system actuator, mechanically coupled to the guidewire and configured for controlling the position of the guidewire, to the vascular introducer sheath and to the reference gantry; displaying position information collected by the system for accurate positioning of a PICC, to a remote operator; navigating the guidewire to the desired position, from commends received from the remote operator; fixing the guidewire in place and advancing the PICC into position over the guidewire.

(14) In a variant of the physician operator workflow for placement of a PICC in patients, the only image documentation of the PICC placement is based on EM position data from the PICC system and relative positioning of the gantry system to the venous introducer sheath.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention relates to a method and system for placing a peripherally inserted central venous catheter (PICC) and positioning the tip accurately in the optimal location within the superior vena cava.

Figure 1:
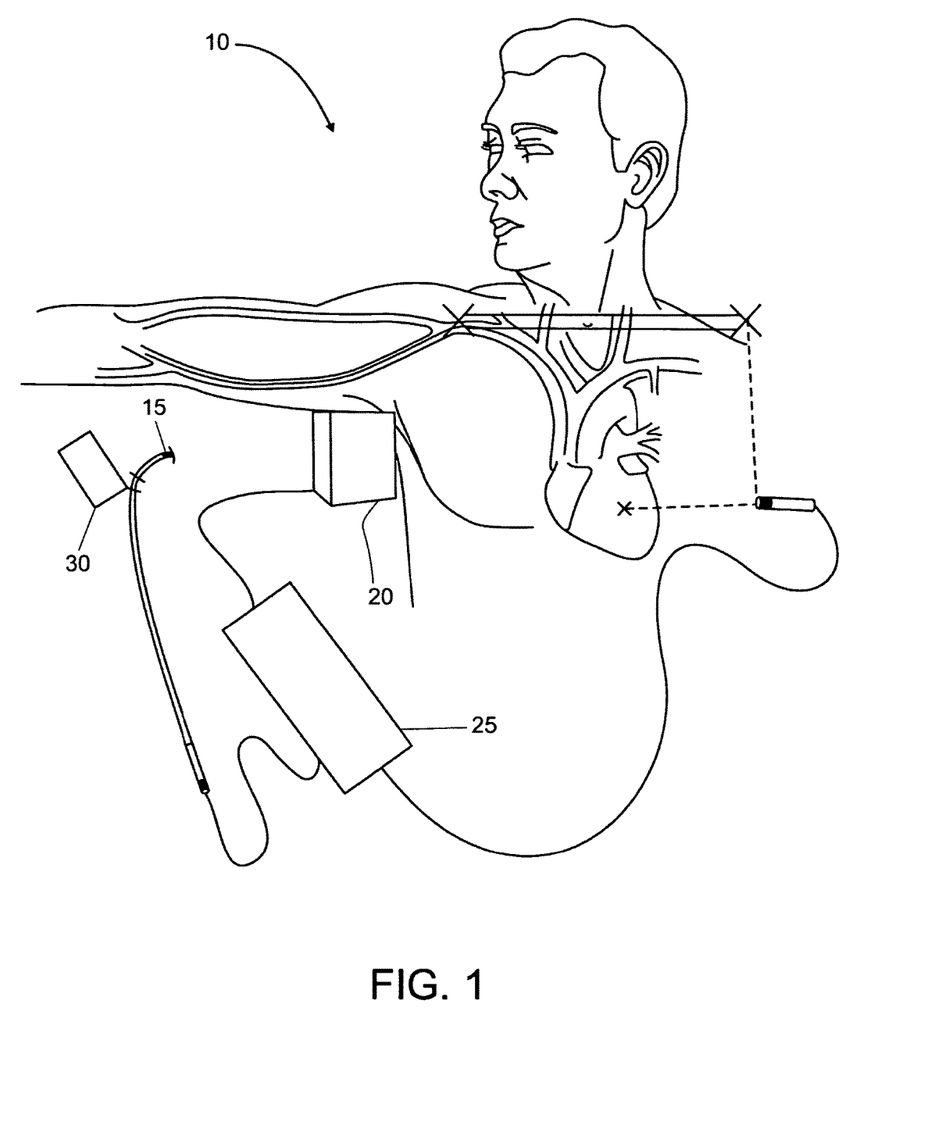
FIG. 1 is a schematic of a system for accurate positioning of a device enabled for endovascular navigation.

An aspect of some embodiments of the present invention relates to system preferably composed of major elements as follows. Referring to FIG. 1, the system 10 has a 3rd generation DC electromagnetic positioning coil 15 and either: a) an EM tracker tip enabled 0.018 in PICC delivery guidewire with angled tip; or b) a guidewire-catheter system with integrated tip sensor coil engineered between the PICC such that the inductor windings are located within the PICC catheter and the magnetic susceptible and magnetic field focusing ferrite core within the guidewire, thereby achieving a separable sensor design to optimize sensor profile (diameter and length) and sensitivity for the PICC procedure. A second component of the system includes an electromagnetic field generator/transmitter mount and position reference gantry 20. A third component of the system is a microcomputer and display 25 with DICOM image output. A fourth component is a servomotor delivery system actuator 30 with a remote operator interface.

The system can use any standard PICC line accepting, for example, a 0.018 in guidewire with a tip tracking sensor mounted within the guidewire tip in its most basic design. In a variant, a more sophisticated design comprises placement of the sensor coil windings into the body of the PICC catheter and positioning the magnetically susceptible sensor (ferrite) core material into a guidewire/steerable introducer mount onto which the PICC catheter is placed. This entire system is manipulated as a unit in the venous system of a patient, and the susceptible core is retracted when the desired position for the PICC is achieved. Use of a valved 5F peel-away vascular introducer sheath allows for a modified workflow with added procedural efficiencies that is outlined below with element 4.

Electromagnetic Positioning Coil Enabled PICC Delivery System and Guidewire Delivery Catheter In a variant, a process for PICC placement in accordance with the present invention, provides an electromagnetic tracker transceiver, such as a 5 or 6-degree of freedom, ferrite core, direct current (DC) electromagnetic tracker coil, placed into the tip of a guidewire. The tracker-tipped guidewire functions as an endoluminal steerable venous probe which is used to enter and deliver a standard 0.018" guidewire to the SVC lumen. The guidewire incorporates at least one tracker at or near the tip. More trackers (2 or more providing 5 or 6 degree of freedom position information) may be incorporated into the body of the guidewire in order to achieve a more accurate guidewire feel to the operator via display of more information on the guidewire shape and stored potential (spring) energy in the catheter body, not simply the tip position. Eventually, the guidewire delivery catheter is removed, leaving the properly positioned guidewire in position and providing the critical depth measurement to which the PICC length is cut (robotically or manually). Then, the appropriate cut-length PICC is advanced over the wire to the target (robotically or manually), the wire is removed, and the line is tested and certified. As a result of the EM sensor guided PICC positioning, an anatomic representation of the central venous anatomy is created. This image representation serves as confirmation of proper positioning, indicating the course to the target and tip location over the image relative to surface anatomical positions.

The guidewire is preferably flexible and manufactured in a range of pre-curved shapes so as to make navigation of the upper extremity anatomy to the SVC junction straightforward. MP and S-curved tips are standard guidewire shapes that will be manufactured, for example.

Figure 2:
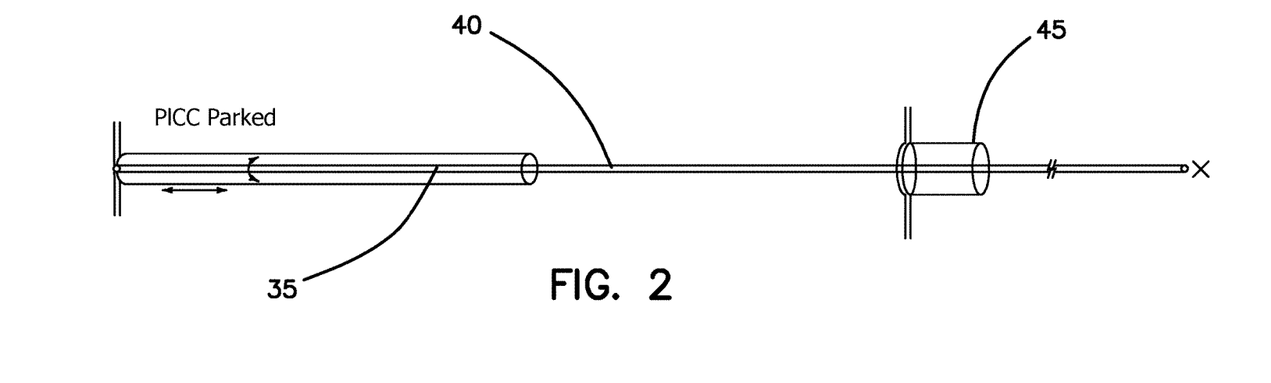
FIGS. 2-4 is a diagram of a device enabled for endovascular navigation in accordance with the principles of the invention.

Referring to FIG. 2, a process for accurate PICC placement comprises:

Electromagnetic Field Generator/Transmitter Mount and Position Reference Gantry

The electromagnetic field generator/transmitter useful for EM guidance systems (such as Ascension Medical Technologies trakSTAR) can be incorporated into a patient position reference gantry, which identifies and localizes anatomic landmarks (including but not limited to the suprasternal notch, xyphoid process of the sternum, the bilateral anterior acromion processes and the T12 spinous process). Thereby, the gantry functions to hold the field generator adjacent to the anatomy of interest including the left or right arm and the thorax while also providing a spatial anatomical localization of reference anatomy for construction of a basic but individual patient specific anthropomorphic model for guidewire delivery catheter navigation overlay in the microcomputer display system. Optionally, the gantry system may also include a wand that can be used to indicate surface anatomic landmarks useful for guidance and creation of the individualized and procedurally unique anthropomorphic model. Isolation and immobilization of the venous sheath relative to the surface anatomical markers is a key design feature of the mount/gantry.

Microcomputer and Display with DICOM Image Output

The gantry based reference anatomy information is used to dynamically track the delivery system (sensor enabled 0.018"guidewire+over the wire PICC, OR, integrated PICC/ sensor coil+guidewire/sensor coil ferromagnetic core) into position in the SVC via operator knowledge of the central venous system standard anatomic configurations as well as through use of cardiogenic impulse motion when the tip nears, enters, or contacts the heart chamber walls. The microcomputer display will provide simulated anterior-posterior and lateral projectional images of the tip position in real time and a time integrated tracing of the tip trajectory over the patient specific anthropomorphic model provided by the electromagnetic field generator mount/anatomic reference gantry. Additional reconstructed spatial data images may be generated to assist the operator. The images may also be used to diagnose conditions such as venous occlusion, venous stenosis and venous anatomic variants.

When the operator achieves satisfactory positioning based on the anatomic references provided by the gantry and guidewire delivery catheter, a reconstructed DICOM image representation of the final catheter trajectory is created to be stored in a picture archiving and communication system (PACS) for medical record documentation and PICC line medical certification.

Servomotor Delivery System Actuator with Remote Operator Interface

The system of the present invention can be used in the standard nursing and/or IR hospital-based venous access triage systems in order to achieve high PICC delivery efficiency and best practice through (1) ionizing radiation use reduction, (2) optimal PICC positioning, and, (3) identification and anatomical imaging based evaluation of those patients who may have complex and challenging anatomy. In order to achieve maximum PICC delivery efficiencies and best practice, the device may optionally have remote operator capabilities.

In a medical workflow scenario, a remote operator driven machine actuator manipulates the delivery guide catheter. The remote operator observes the microcomputer display from his or her location in real-time. The PICC placement machine consists of linear and rotary actuators and linear and rotary position encoders that are mechanically coupled to the PICC delivery guidewire or PICC+sensor coil array and ferromagnetic sensor core+guidewire in a sterile manner. A robust telecommunication platform based on an internal hospital intranet or a secure internet links the operator to the machine actuator.

In another variant, a preferred single physician operator workflow is further outlined as follows. The physician makes access rounds and visits each PICC patient and a valved, 5-French peel away vascular introducer sheath is placed into the brachial, basilic or other vein at bedside and this sheath is blocked with heparin for later access during PICC guidewire delivery catheter placement. It is estimated that 10 patients can be accessed with a valved, 5-french vascular introducer sheath in 30 minutes by a single physician using ultrasound guidance. Next, the machine is wheeled to the individual patient rooms serially while the physician reports to a reading room to perform clinical radiological duties at an imaging workstation. A nurse or technician then positions and prepares the patients for the guidewire delivery catheter placement sequentially. The machine actuator is mechanically linked to the vascular introducer sheath and positioning gantry. The position information, obtained through the system is then used by the physician at the remotely located clinical workstation. A representation of the anatomy is provided to the operator whose task is to navigate (through rotation and advancement/retraction of the guidewire+PICC or PICC guidewire/ sensor delivery system to achieve optimal position, which is defined as an eventual positioning of the guidewire tip in the SVC. Once the guidewire is in proper anatomic position, the nurse or technician places and/or pins the standard 0.018" guidewire in position and removes the delivery guide catheter and advances the PICC into position over the guidewire. In preferred embodiments, trimming the PICC and advancing it into position are achieved robotically. In the ultimate final step, the line is tested by the nurse or technician and secured in position. If the line functions appropriately (demonstrates venous blood return and flushes saline with normal resistance), the line is deemed ready for use with no further confirmatory imaging required. The only image documentation is based on the EM guidance system and relative positioning of the gantry system to the venous introducer sheath.

In other variants of the invention, intravenous-catheter-adapted remote sensors (often fiber-optic and sensitive to pressure, color, doppler blood velocity, blood oxygenation level, and microarray sensors designed to bind and electronically indicate circulating proteins) may be incorporated into the system to add functionality. Furthermore, the technique may be extended to placement of other devices besides PICC, such as Swan Ganz catheters, angioplasty balloons, stents, ultrasound imaging probes and optical scanners.

FIG. 1 is an outline of one embodiment of the PICC positioning system. Placement of the electromagnetic field generator (for example, pulsed DC) in the patient axilla and the position of the patient and key anatomic landmarks of the sternum, xyphoid process, manubrium, sternal notch, clavicles and acromion processes are depicted. The patient is depicted in the ideal procedural position. The guidewire delivery catheter could encompass any tool enabled for endovascular navigation, specifically a PICC catheter, and, more broadly any device which is manipulated in over the wire or monorail fashion. These are the two mainstay techniques employed in endovascular surgical procedures.

In a variant, referring to FIG. 2, a PICC catheter 35 is configured with an EM sensor tip 0.018 in guidewire 40 enclosed in a circular track external sheath (not shown) that is contained in a sterile enclosure 45 (partially shown). The external sterile track must measure 140 cm to accommodate a 70 cm insertion length (an uncut 70 cm PICC catheter). Other catheter types and lengths can be used, but, the external sterile enclosure for the catheter guidewire may be two times the catheter length. The PICC or other catheter may be kept external to the body while the free guidewire is manipulated through the anatomy via rotational and translational actuators through the sterile enclosure. When the guidewire achieves the target, the catheter can be advanced independently from the guidewire and over the guidewire to place the tip at the target. In other embodiments, an independent rotational actuator can be employed in order to achieve more complex catheter+guidewire manipulations that are required in many endovascular surgical procedures. FIG. 2 illustrates linear+rotary actuators of a PICC guidewire for navigating the guidewire to target. A PICC is parked in the external sterile enclosure that has linear and rotational actuators built in.

Figure 3:
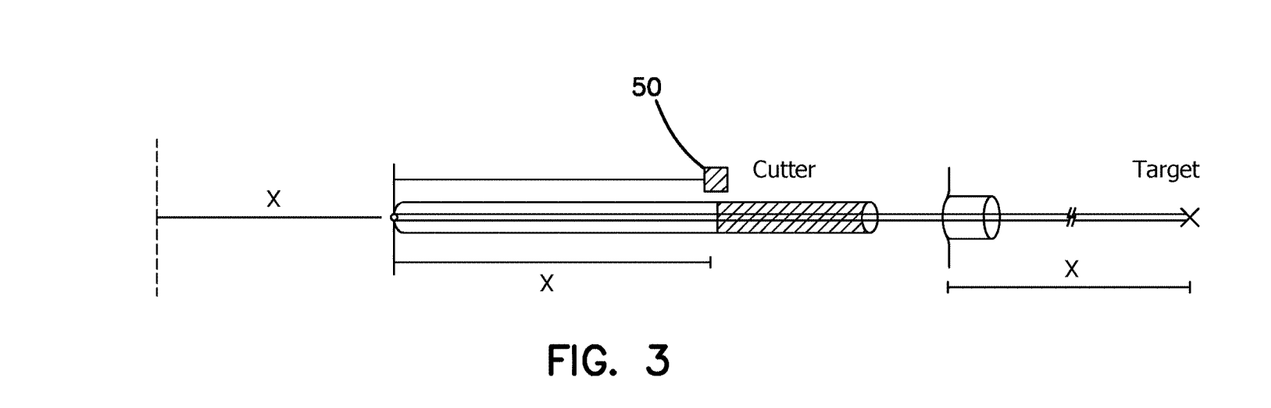

Referring to FIG. 3, a desired target position is obtained with the guidewire tip via a sequence of rotational and translational actuations of the guidewire within the lumen of the venous anatomy. A PICC length is calculated as inserted distance x. For example 0-70 cm. The parked PICC must be trimmed to length x. A cutter 50 is advanced over the parked PICC to x and activated, cutting the PICC to length x while it is in position on the guidewire. The excess shaded material is removed by a grasper mechanism which retracts the excess catheter material over a longitudinally oriented blade which splits the lumen of the excess catheter material thereby freeing it from the guidewire.

Figure 4:
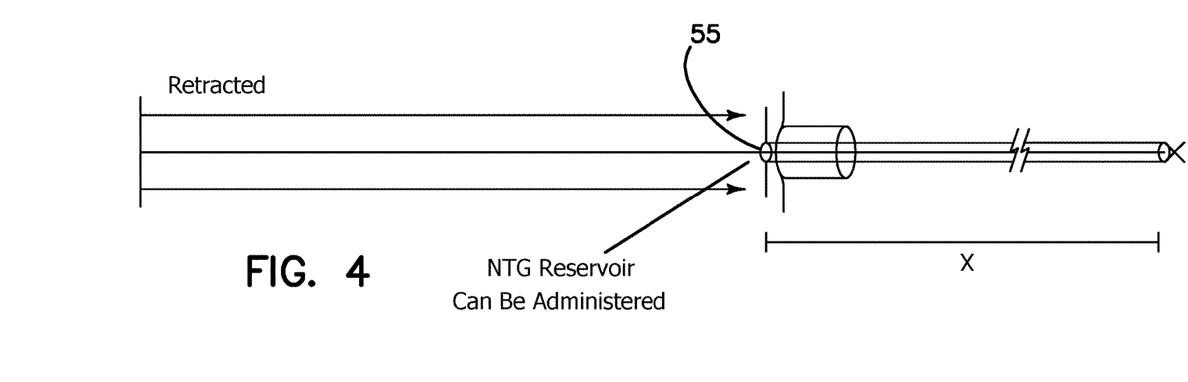
Figure 7:
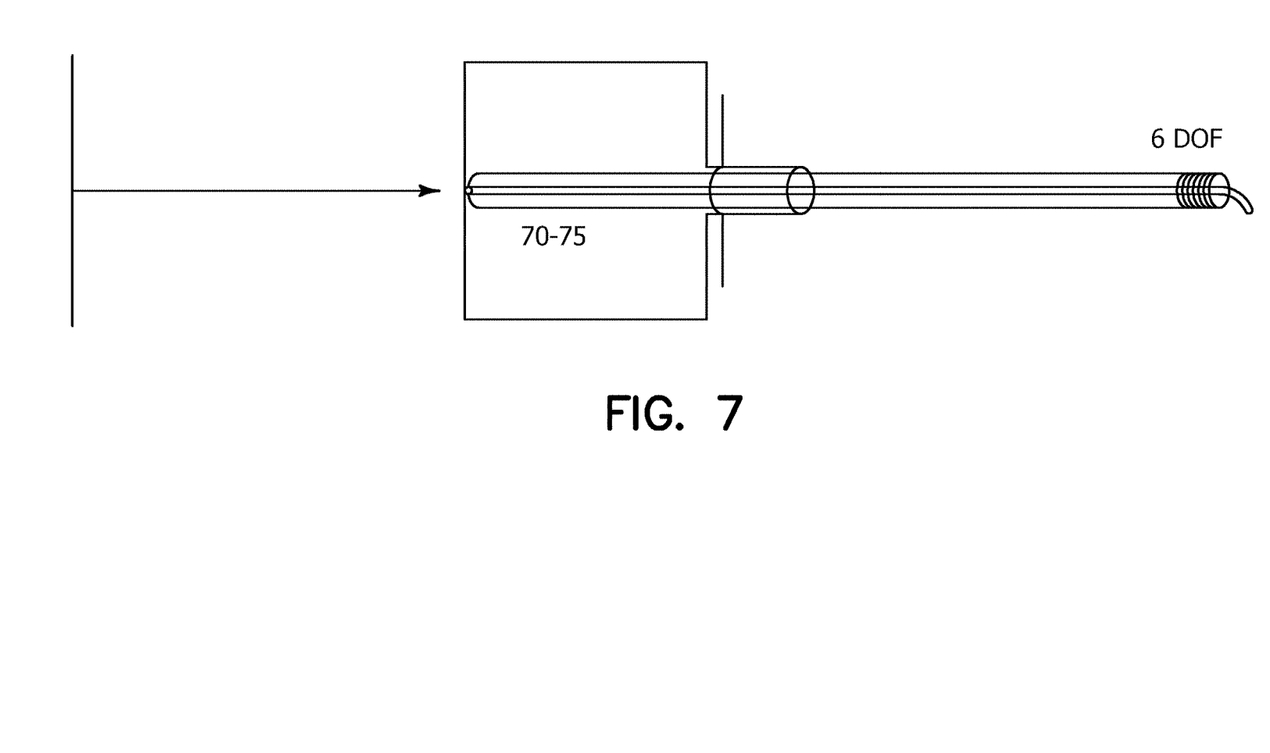

Referring to FIGS. 4 and 7, the trimmed PICC is advanced to target over guidewire and the guidewire is then retracted. Optionally, an NTG (or other drug containing) reservoir 55 can be coupled to the free PICC lumen (in a dual lumen PICC, for instance) and this lumen can be utilized to administer nitroglycerin through second lumen to threat venospasm or to provide additional hydrostatic lubrication/cushioning to the catheter tip as it is advanced to the target. A number of other pharmacomechanical treatments could be delivered through a multilumen catheter system such as suction thrombectomy or drug lacing of thrombus or drug/embolic delivery into target anatomy via arteries/veins or radiographic contrast administration for diagnostic imaging (digital subtraction fluoroscopy, for instance). Balloons and stents optionally may be actuated via a non wire containing lumen.

Figure 5:
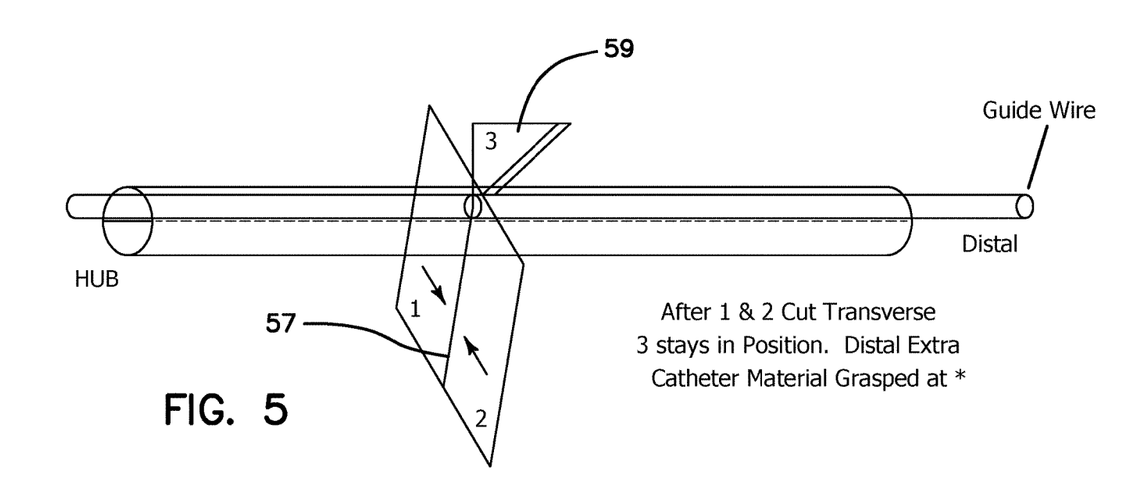
FIG. 5 is a diagram of a cutter mechanism.

In another variant, referring to FIG. 5 a PICC cutter has two blades 57 that enclose the guidewire for cutting the catheter, and an optional third blade 59 which splits longitudinally the catheter lumen enclosing the guidewire, thereby allowing the extra catheter material to be pulled free from the wire with minimal mechanical tension placed on the wire transverse to its longitudinal axis. Mechanical blades are described, however focused heating elements or chemical applicators could be employed to sever the catheter material and achieve the goals of PICC cutting/freeing from the guidewire.

Figure 6:
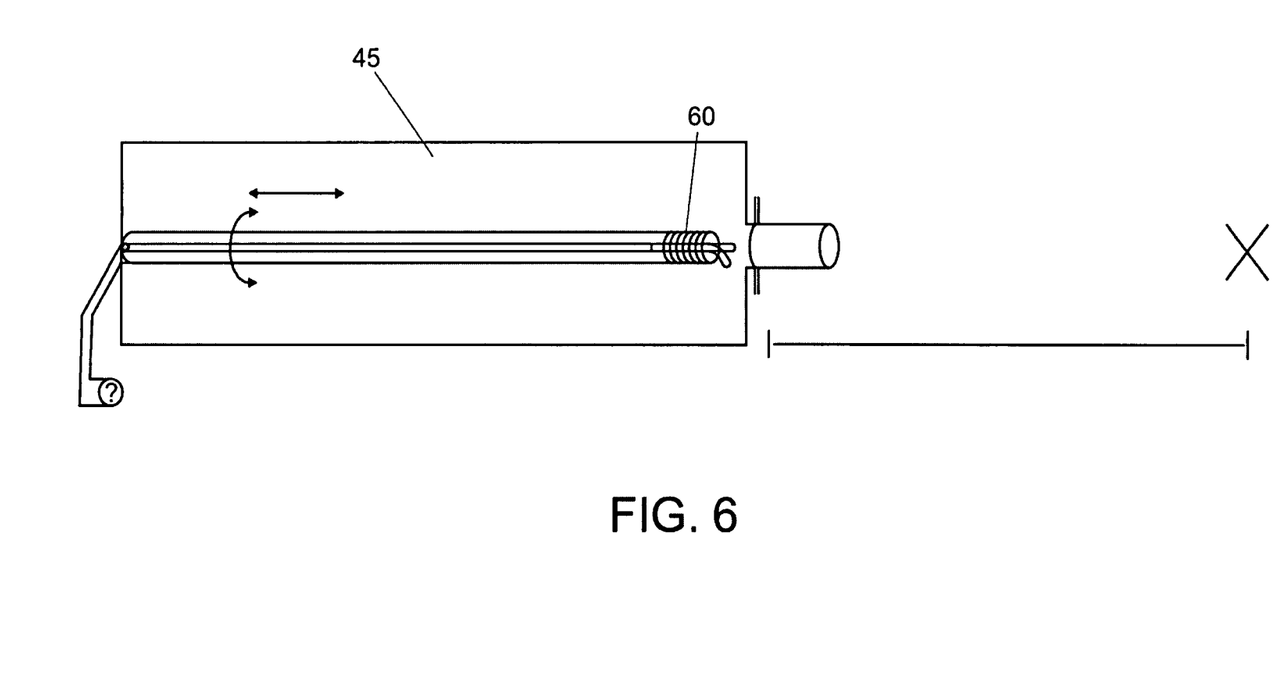
FIGS. 6-7 is a diagram of a device enabled for endovascular navigation in accordance with the principles of the invention.

In a further variant, referring to FIG. 6, a sensor coil 60 is integrated into the PICC body/tip. A hemostatic (fluid tight) connector hub creation that is ideally power injectable (able to withstand 300-1000 PSI pressure) and thereby provides an individually custom fitted and power injectable for CT contrast administration PICC for the patient. The hub connector is typically a common luer lock fitting that is universally used in medical intravenous lines including PICC.

The distal sensor tip could be 6 degrees of freedom (x,y,z coordinate position plus additional rotational yaw-attitude positions) or 5 degrees of freedom (coordinate position only). 5 degrees of freedom (DOF) sensors require fewer leads and coils and are generally more compact. The 5 DOF sensors could provide a limited virtual 6 DOF readout via the required coupling to the rotational actuator, which will provide a motor position reference.

In a variant, the hub with luer lock fitting is bonded to the cut sensor integrated PICC. In this embodiment, the PICC catheter is cut from the back end and this requires that the luer lock fitting be bonded to the catheter body. Once the catheter is cut, the leads to the sensor coil array are cut, thereby disabling the distal tip sensor coil. In some embodiments, the bonded luer lock hub incorporates electrical lead coupling to the sensor windings thereby allowing for continued sensor use in navigation.

The system and method of the present invention has several advantages. There is no need for post-procedural chest radiographs to confirm PICC positioning. Correct placement will be achieved >95% of the time versus ~15% using current nursing methods. Furthermore, the 5% of failures will successfully identify and provide imaging information on those patients in whom standard interventional radiology (IR) placement techniques for PICC or alternative strategies for central venous access will be technically required due to hostile patient anatomy. The additional imaging information can be used to improve the efficiency of subsequent procedures through anatomic representation of the peripheral and central venous anatomy that presented the challenge (the obstruction to intralumenal passage). This allows for improved process efficiencies through anatomic representation of the hostile anatomy for the second placement operator. The system is fully portable and can be employed to perform the PICC placement procedure at the patient's bedside. As an option, the intravascular positioner/delivery system portion of the device may be controlled remotely to perform the key step of navigating to the SVC. This allows maximum physician participation in the PICC placement procedure with a high degree of flexibility of workflow, representing an advantage to physician operators, individual patients, hospital systems and payors.

The device as outlined above would provide a significant cost savings to the entire medical system through major medical system efficiency gains in venous vascular access management. The device represents a novel application of EM guidance technology to the specific medical procedure of PICC placement. The device description outlines a method for intravascular guide manipulation that has relevance to numerous other procedures including intravascular, intra-biliary and intra-enteric tool manipulations among others where internal anatomic structures are predictably located in reference to external surface anatomy, and, procedural guidance can be achieved through an electronic operator interface that demonstrates in vivo tool position relative to a set of relevant surface anatomy reference points. A natural outcome of manipulation of the EM tracking probe inside the human body with reference to surface anatomic positions is the creation of a detailed image defining endoluminal boundaries (including but not limited to internal boundaries of arterial walls, venous walls, and biliary walls). This imaging technique can be used for medical diagnostic purposes as well as for procedural tool localization While various embodiments of the present invention have been described above, it should be understood that they have been presented by way of example only, and not of limitation Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A system for accurate positioning of a device enabled for endovascular navigation, comprising:
    one of a catheter or guidewire or combination for navigating through a patient's vasculature, comprising an electromagnetic (EM) based tracking component at or near the leading end of the device;
    an EM positioning field generator configured on a reference gantry;
    a computer and display configured to output position information of the leading end of one of a guidewire or a catheter or a combination thereof; and
    a servomotor delivery system actuator, mechanically coupled to the one of a guidewire or catheter or combination thereof, and configured for controlling the position the guidewire or catheter or combination thereof; and
wherein: the servomotor delivery system actuator, the mechanical coupling to the guidewire or catheter, or combination thereof, is sealed within a sterile enclosure; and wherein the entire guidewire or catheter or combination thereof is housed within the sterile enclosure.

2. The system for accurate positioning of a device enabled for endovascular navigation of claim 1, wherein the device comprises a peripherally inserted central venous catheter (PICC).

3. The accurate PICC positioning system of claim 2, wherein the one of a catheter or guidewire or combination comprises a guidewire comprising an EM tracker tip with having an angled guidewire tip.

4. The accurate positioning system of claim 3 wherein the EM positioning field generator configured on a reference gantry is configured to identify and localize anatomic landmarks.

5. The accurate positioning system of claim 1, wherein the one of a catheter or guidewire or combination comprises a guidewire-catheter system having an integrated tip sensor coil engineered between the catheter and the guidewire such that inductor windings are located within the catheter; and a magnetically susceptible and magnetic field focusing ferrite core is disposed within the guidewire.

6. The accurate positioning system of claim 1, wherein the servomotor has a remote operation interface, configured to receive and carry out commands from a remote location, to manipulate the guidewire and catheter.

7. The accurate PICC positioning system of claim 1, wherein the EM tracking component comprises a sensor coil integrated into the tip of a PICC, comprising:
    a power injectable hemostatic connector hub for contrast administration through the PICC.

8. The accurate positioning system of claim 1, wherein the system is configured to record anatomy shape data, during placement of the catheter.

9. The accurate positioning system of claim 1, further comprising an intravenous catheter-adapted remote sensor.

10. The accurate positioning system of claim 1 wherein the EM positioning field generator configured on a reference gantry is configured to identify and localize anatomic landmarks.

11. The accurate positioning system of claim 10 wherein the reference gantry further comprises a wand that can be used to indicate surface anatomic landmarks useful for guidance and creation of an individualized and procedurally unique anthropomorphic model.

12. The accurate positioning system of claim 10 wherein the EM tracking component comprises a sensor coil integrated into the tip of a PICC.

13. The accurate positioning system of claim 1 comprising an electromagnetic tracker transceiver disposed in a tip of the guidewire.

* * * * *